United States Patent
Westwood et al.

(10) Patent No.: US 8,497,291 B2
(45) Date of Patent: Jul. 30, 2013

(54) CRYSTALLINE PYRIMIDINE NUCLEOSIDE DERIVATIVE SUSPENSIONS IN CAPSULES

(75) Inventors: Robert Westwood, Oxford (GB); Alistair Selkirk, Dundee (GB)

(73) Assignee: Cyclacel Limited, London (GB)

( * ) Notice: Subject to any disclaimer, the term of this patent is extended or adjusted under 35 U.S.C. 154(b) by 1016 days.

(21) Appl. No.: 12/097,912

(22) PCT Filed: Dec. 22, 2006

(86) PCT No.: PCT/GB2006/004927
§ 371 (c)(1),
(2), (4) Date: Sep. 19, 2008

(87) PCT Pub. No.: WO2007/072061
PCT Pub. Date: Jun. 28, 2007

(65) Prior Publication Data
US 2009/0074856 A1  Mar. 19, 2009

(30) Foreign Application Priority Data
Dec. 23, 2005 (GB) .................................. 0526419.7

(51) Int. Cl.
*A01N 43/80* (2006.01)
*A61K 31/42* (2006.01)
*A61K 9/64* (2006.01)
(52) U.S. Cl.
USPC ......................................... 514/378; 424/456

(58) Field of Classification Search
USPC .......................................... 514/378; 424/456
See application file for complete search history.

(56) References Cited

U.S. PATENT DOCUMENTS

| 5,591,607 | A | * | 1/1997 | Gryaznov et al. | ............ 435/91.1 |
| 5,688,949 | A | * | 11/1997 | Inoue et al. | .................... 544/281 |
| 5,952,383 | A | * | 9/1999 | Metziger et al. | .............. 514/569 |
| 2003/0124182 | A1 | * | 7/2003 | Shojaei et al. | ................. 424/451 |
| 2004/0053883 | A1 | * | 3/2004 | Takita et al. | .................... 514/50 |

FOREIGN PATENT DOCUMENTS

| EP | 0536936 A1 | 4/1993 |
| EP | 1364959 A1 | 11/2003 |
| WO | WO-2005/123061 A1 | 12/2005 |

OTHER PUBLICATIONS

International Search Report for Application No. PCT/GB2006/004927, dated Aug. 6, 2007.
Written Opinion for Application No. PCT/GB2006/004927, dated Aug. 6, 2007.

* cited by examiner

*Primary Examiner* — Benjamin Packard
(74) *Attorney, Agent, or Firm* — Nelson Mullins Riley & Scarborough LLP; Jane E. Remillard, Esq.; Cynthia L. Kanik

(57) ABSTRACT

The present invention relates to a pharmaceutical formulation which comprises (i) a capsule, and (ii) a core comprising crystalline 2'-cyano-2'-deoxy-$N^4$-palmitoyl-1-$\beta$-D-arabinofuranosylcytosine and a liquid carrier.

19 Claims, No Drawings

CRYSTALLINE PYRIMIDINE NUCLEOSIDE DERIVATIVE SUSPENSIONS IN CAPSULES

RELATED APPLICATIONS

The present application is a 35 U.S.C. 371 national stage filing of International Application No. PCT/GB2006/004927, filed Dec. 22, 2006, which claims priority to Great Britain Application No. 0526419.7, filed Dec. 23, 2005. The entire contents of each of these applications are hereby incorporated herein by reference in their entirety.

FIELD OF THE INVENTION

The present invention relates to a new pharmaceutical formulation. More specifically, the invention provides a new capsule formulation for a pyrimidine nucleoside derivative, 2'-cyano-2'-deoxy-$N^4$-palmitoyl-1-β-D-arabinofuranosylcytosine, which is therapeutically useful in the treatment and/or prevention of cancer.

BACKGROUND TO THE INVENTION

The therapeutic use of pyrimidine nucleosides in the treatment of proliferative disorders has been well documented in the art. By way of example, commercially available antitumor agents of the pyrimidine series include 5-fluorouracil (Duschinsky, R., et al., J. Am. Chem. Soc., 79, 4559 (1957)), Tegafur (Hiller, S A., et al., Dokl. Akad. Nauk USSR, 176, 332 (1967)), UFT (Fujii, S., et al., Gann, 69, 763 (1978)), Carmofur (Hoshi, A., et al., Gann, 67, 725 (1976)), Doxyfluridine (Cook, A. F., et al., J. Med. Chem., 22, 1330 (1979)), Cytarabine (Evance, J. S., et al., Proc. Soc. Exp. Bio. Med., 106. 350 (1961)), Ancytabine (Hoshi, A., et al., Gann, 63, 353, (1972)) and Enocytabine (Aoshima, M., et al., Cancer Res., 36, 2726 (1976)).

EP 536936 (Sankyo Company Limited) discloses various 2'-cyano-2'-deoxy-derivatives of 1-β-D-arabinofuranosylcytosine which have been shown to exhibit valuable anti-tumour activity. One particular compound disclosed in EP 536936 is 2'-cyano-2'-deoxy-$N^4$-palmitoyl-1-β-D-arabinofuranosylcytosine (referred to hereinafter as "CYC682"); this compound is currently under further investigation.

CYC682, also known as 1-(2-C-cyano-2-dioxy-β-D-arabino-pentofuranosyl)-$N^4$-palmitoyl cytosine, (Hanaoka, K., et al, Int. J. Cancer, 1999:82:226-236; Donehower R, et al, Proc Am Soc Clin Oncol, 2000: abstract 764; Burch, Pa., et al, Proc Am Soc Clin Oncol, 2001: abstract 364), is an orally administered novel 2'-deoxycytidine antimetabolite prodrug of the nucleoside CNDAC, 1-(2-C-Cyano-2-deoxy-β-D-arabino-pentafuranosyl)-cytosine.

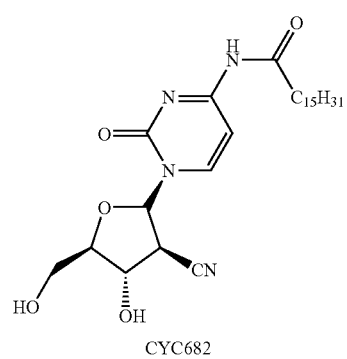

CYC682

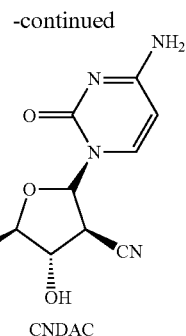

CNDAC

CYC682 has a unique mode of action over other nucleoside metabolites such as gemcitabine in that it has a spontaneous DNA strand breaking action, resulting in potent anti-tumour activity in a variety of cell lines, xenograft and metastatic cancer model.

CYC682 has been the focus of a number of studies in view of its oral bioavailability and its improved activity over gemcitabine (the leading marketed nucleoside analogue) and 5-FU (a widely-used antimetabolite drug) based on preclinical data in solid tumours. Recently, investigators reported that CYC682 exhibited strong anticancer activity in a model of colon cancer. In the same model, CYC682 was found to be superior to either gemcitabine or 5-FU in terms of increasing survival and also preventing the spread of colon cancer metastases to the liver (Wu M, et al, Cancer Research, 2003: 63:2477-2482). To date, phase I data from patients with a variety of cancers suggest that CYC682 is well tolerated in humans, with myelosuppression as the dose limiting toxicity.

A number of different formulations of CYC682 have been investigated to date. Prior art formulations have typically involved granulate powder fill capsules prepared using the active agent in amorphous form. However, these formulations were difficult to manufacture and led to capsules containing varying amounts of crystalline material formed as a result of water absorption during the formulation process. As a consequence, these capsules exhibited poor stability and required storage at low temperature (4° C.).

The present invention seeks to provide a new formulation of CYC682 that alleviates one or more of the problems associated with the prior art formulations investigated to date. In particular, the present invention seeks to provide a formulation for CYC682 which allows for easier processing and which results in capsules exhibiting improved stability.

STATEMENT OF INVENTION

A first aspect of the invention relates to a pharmaceutical formulation which comprises (i) a capsule, and (ii) a core comprising crystalline 2'-cyano-2'-deoxy-$N^4$-palmitoyl-1-β-D-arabinofuranosylcytosine and a liquid carrier.

Advantageously, the claimed formulation exhibits improved stability and can be stored at room temperature, compared to 4° C. for the prior art powder fill formulations. Furthermore, preliminary studies indicate that the liquid fill formulation allows equivalent absorption of the active agent into the bloodstream and, in the case of human dosing, shows similar pharmacodynamic effects. Finally, the process for preparing the claimed formulation has manufacturing advantages in that it minimises the handling of the cytotoxic active agent in the powder form since once the mixing has taken place, all filling processes involve liquid handling without the need for extensive containment.

A second aspect of the invention relates to the use of a medium chain triglyceride as a liquid carrier in capsules of crystalline 2'-cyano-2'-deoxy-$N^4$-palmitoyl-1-β-D-arabinofuranosylcytosine.

A third aspect relates to a liquid carrier for use in capsules of crystalline 2'-cyano-2'-deoxy-$N^4$-palmitoyl-1-β-D-arabinofuranosylcytosine, wherein the liquid carrier is fractionated coconut oil or caprilyic/capric triglyceride.

A fourth aspect of the invention relates to a process for preparing the above-described pharmaceutical formulation which comprises the steps of:
(i) admixing crystalline 2'-cyano-2'-deoxy-$N^4$-palmitoyl-1-β-D-arabino-furanosylcytosine and a medium chain triglyceride to form a suspension;
(ii) transferring the mixture formed in step (i) into a pre-formed capsule; and
(iii) sealing the capsule.

DETAILED DESCRIPTION

As mentioned above, in a first aspect, the invention provides a new pharmaceutical formulation of 2'-cyano-2'-deoxy-$N^4$-palmitoyl-1-β-D-arabinofuranosylcytosine which is in the form of a liquid filled capsule.

More specifically, the pharmaceutical formulation comprises (i) a capsule, and (ii) a core comprising crystalline 2'-cyano-2'-deoxy-$N^4$-palmitoyl-1-β-D-arabino-furanosylcytosine and a liquid carrier.

Preferably, the pharmaceutical formulation is for oral administration.

Capsule

The pharmaceutical composition of the present invention comprises an outer capsule or shell which is capable of encapsulating the liquid core.

Suitable capsule materials will be familiar to the person skilled in the art and include, for example, any polymeric material (polymers or copolymers, natural or synthetic) possessing the desired physical characteristics to allow delivery of the active agent by oral administration.

By way of example, suitable capsules include those prepared from water-soluble cellulose derivatives, a gelling agent and a co-gelling agent (see for example, U.S. Pat. No. 5,431,917). Other examples include capsules prepared from hydroxypropyl methylcellulose and an ammonium salt of cellulose acetate phthalate polymer, or capsules prepared from gelatin and an ammonium salt of a copolymer of methacrylic acid and methacrylic acid alkyl ester.

Further examples include polymers obtainable by the polymerization of at least one vinyl ester in the presence of one or more polyether-containing compounds and, where appropriate, one or more other copolymerizable monomers (see for example, U.S. Pat. No. 6,783,770).

Other suitable capsule materials include polymers or copolymers obtained by polymerizing or copolymerizing at least one polymerizable vinyl monomer in the presence of polyvinyl alcohol and/or derivatives thereof (see for example, US20050186268). Unlike conventional capsules, hard capsules of this type are compatible with liquid or semi-liquid cores.

Preferably, the capsule is a hard capsule, although soft capsules can also be used.

In one preferred embodiment, the capsule is a gelatin capsule, more preferably a hard gelatin capsule. The gelatin capsules according to the invention may be prepared using conventional techniques (see eg. The Theory and Practice of Industrial Pharmacy, Ed. Lachman L. et al., Third Edition, Lea & Febiger, 1986, Philadelphia, pp. 398-412).

In one particularly preferred embodiment, the gelatin capsule comprises one or more opacifying agents and/or one or more pigments.

Preferably, the pigments and/or opacifying agents are each present in an amount of about 0.1 to about 10% by weight.

Suitable pigments include, for example, titanium dioxide, laked pigments (e.g. FS&C aluminium lakes or D&C lakes), iron oxide pigments, natural colorants, synthetic oxides or the like, or a dyestuff selected from indigo, carmine, quinoline yellow, orange yellow S, curcurmin, riboflavin and cochineal.

An especially preferred opacifying agent is titanium dioxide. More preferably, the titanium dioxide is present in an amount of about 2%.

In addition, the capsule material may also contain other additives. These include, but are not limited to, absorbents, acids, adjuvants, anticaking agent, glidants, antitacking agents, antifoamers, anticoagulants, antimicrobials, antioxidants, antiphlogistics, astringents, antiseptics, bases, binders, chelating agents, sequestrants, coagulants, coating agents, colorants, dyes, pigments, compatiblizers, complexing agents, softeners, crystal growth regulators, denaturants, dessicants, drying agents, dehydrating agents, diluents, dispersants, emollients, emulsifiers, encapsulants, enzymes, fillers, extenders, flavor masking agents, flavorants, fragrances, gelling agents, hardeners, stiffening agents, humectants, lubricants, moisturizers, bufferants, pH control agents, plasticizers, soothing agents, demulcents, retarding agents, spreading agents, stabilizers, suspending agents, sweeteners, disintegrants, thickening agents, consistency regulators, surfactants, opacifiers, polymers, preservatives, antigellants, rheology control agents, UV absorbers, tonicifiers and viscomodulators. One or more additives from any particular class, as well as one or more different classes of additives, may be present in the compositions. Specific examples of additives are well known in the art. Preferred additives include surfactants and polymers.

In one particularly preferred embodiment, the gelatin capsule is sealed by a gelatin band.

Liquid Carrier

As mentioned above, the formulation of the invention comprises a liquid or semi-liquid core comprising 2'-cyano-2'-deoxy-$N^4$-palmitoyl-1-β-D-arabinofuranosyl-cytosine (referred to herein as the active agent) and a liquid carrier.

Preferably, substantially all the active agent is suspended in the liquid carrier. However, in some cases, the active agent may be partially solubilized and partially suspended in the liquid carrier.

In one particularly preferred embodiment, the active agent is suspended in the liquid carrier.

In another embodiment, the active agent is partially or fully dissolved in the liquid carrier.

In one particularly preferred embodiment, the liquid carrier is a medium chain triglyceride oil.

In one highly preferred embodiment, the medium chain triglyceride is fractionated coconut oil or caprilyic/capric triglyceride. Commercially available Myglyol 812N is particularly preferred.

At room temperature, Myglyol 812N (also known as MCT, DAC, oleum neutrale, CTFA, caprilyic/capric triglyceride (caprylic acid: $C_8$, capric acid: $C_{10}$)) is a liquid lipid oil of low viscosity. Usually, MCT fatty acid composition is dominated by C8 fatty acids (50 to 65%), followed by $C_{10}$ (30 to 45%), $C_{12}$ (max 5%) and $C_6$ (max 3%). The oil is know to be more biodegradable than lipids with longer fatty acid chains. Due to the absence of toxicity on skin and mucous membranes, MCT has applications in dermal products where it enhances permeation and spreading. MCT is also widely used in oral formulations as a lubricant and drug solvent, and as a solution enhancer in parenteral formulations.

In an alternative embodiment, the liquid carrier comprises polyglycolized glycerides, for example, Gelucire®.

Gelucire compositions are inert semi-solid waxy materials which are amphiphilic in character and are available with varying physical characteristics. They are surface active in nature and disperse or solubilize in aqueous media forming micelles, microscopic globules or vesicles. They are identified by their melting point/HLB value. The melting point is expressed in degrees Celsius and the HLB (Hydrophile-Lipophile Balance) is a numerical scale extending from 0 to approximately 20. Lower HLB values denote more lipophilic and hydrophobic substances, and higher values denote more hydrophilic and lipophobic substances. The affinity of a compound for water or for oily substances is determined and its HLB value is assigned experimentally. One or a mixture of different grades of Gelucire excipient may be chosen to achieve the desired characteristics of melting point and/or HLB value.

Preferred Gelucires for use in the present invention include Gelucire® 44/14, 53/10, 50/13, 42/12, and 35/10 from the Gaftefossé company.

Gelucire 50/13 compositions are polyglycolized glycerides that are prepared by the alcoholysis reaction of natural oils with polyethylene glycols (PEG). They are mixtures of monoesters, diesters and/or triesters of glycerides of long chain ($C_{12}$ to $C_{18}$) fatty acids, and PEG (mono- and/or di-) esters of long chain ($C_{12}$ to $C_{18}$) fatty acids and can include free PEG. Gelucire compositions are generally described herein as fatty acid esters of glycerol and PEG esters or as polyglycolized glycerides.

The large family of Gelucire compositions is characterized by a wide range of melting points of from about 33° C. to about 64° C. and most commonly from about 35° C. to about 55° C., and by a variety of HLB values of from about 1 to about 14, most commonly from about 7 to about 14. For example, Gelucire 50/13 designates a melting point of approximately 50° C. and an HLB value of about 13 to this grade of Gelucire. The appropriate choice of melting point/HLB value of a Gelucire or a mixture of Gelucire compositions will provide the delivery characteristics needed for a specific function, e.g., immediate release, sustained release, and the like. The low melting points of many of the solid Gelucire compositions provide a means of incorporating the pharmaceutically active ingredients in them at temperatures from about 0° C. to about 50° C. above their respective melting points, and then filling the melt (solution and/or dispersion) in hard gelatin capsules. The melt solidifies inside the capsules upon cooling to room temperature.

In one highly preferred embodiment of the invention, the liquid carrier comprises Gelucire 44/14. This carrier is a semi-solid excipient which is a mixture of glycerol and PEG1500 esters of long chain fatty acids. The suffixes 44 and 14 refer to its melting point and hydrophilic/lipophilic balance (HLB) respectively. Gelucire 44/14 is commercially available (CAS121548-04-7) and is also known as PEG 32 glycerol laurate.

Gelucire 44/14 and Miglyol 812N can be used either alone, or in combination with one or more other co-carriers or additives. In one preferred embodiment, Miglyol 812N is used in combination with colloidal silicon dioxide (Aerosil 200). Preferably, the Miglyol 812N is used with up to 2% combination colloidal silicon dioxide.

Advantageously, formulations comprising Myglyol 812N and Gelucire 44/14 both show excellent stability superior to other formulations. Myglyol 812N is particularly preferred as the liquid carrier in view of its more favourable viscosity properties.

In one embodiment of the invention, the core may further comprise additional ingredients, for example, one or more vegetable oils, especially arachidis oil or sesame oil, or other pharmaceutically acceptable diluents, excipients or carriers. The core may also contain one or more solubilisers, one or more surfactants and/or one or more co-surfactants. A preferred solubilizer is diethylene glycol monoethyl ether. Preferred surfactants include caprylocaproyl macrogolglycerides or polyoxyethylene castor oil derivatives. Particularly preferred polyoxyethylene castor oil derivatives are polyoxyl (40) hydrogenated castor oil or polyoxyl (35) hydrogenated castor oil. A preferred co-surfactant is polyethylene glycol 400. A preferred viscosity imparter is polyvinylpyrrolidone. A particularly preferred viscosity imparter is povidone (PVP K-30).

Other examples of additional ingredients include colloidal silicon dioxide (for example, Aerosil 200), Gelucire 44/11, PEG4005, Polyoxamers188 and 124, Lipoid PPL, Captex 200 and Labrafil.

In one preferred embodiment, the core consists essentially of crystalline 2'-cyano-2'-deoxy-$N^4$-palmitoyl-1-β-D-arabinofuranosylcytosine and the liquid carrier.

In a more preferred embodiment, the core consists of 2'-cyano-2'-deoxy-$N^4$-palmitoyl-1-β-D-arabinofuranosylcytosine and the liquid carrier alone, i.e. no other ingredients are present.

In one preferred embodiment, the amount of liquid carrier is from 1 to 50 parts by weight relative to 1 part by weight of the crystalline 2'-cyano-2'-deoxy-$N^4$-palmitoyl-1-β-D-arabinofuranosylcytosine.

In one preferred embodiment, the amount of liquid carrier is from 2 to 50 parts by weight relative to 1 part by weight of the crystalline 2'-cyano-2'-deoxy-$N^4$-palmitoyl-1-β-D-arabinofuranosylcytosine.

In a more preferred embodiment, the amount of liquid carrier is from 1 to 10 parts by weight relative to 1 part by weight of the crystalline 2'-cyano-2'-deoxy-$N^4$-palmitoyl-1-β-D-arabinofuranosylcytosine.

In a more preferred embodiment, the amount of liquid carrier is from 2 to 10 parts by weight relative to 1 part by weight of the crystalline 2'-cyano-2'-deoxy-$N^4$-palmitoyl-1-β-D-arabinofuranosylcytosine.

In an even more preferred embodiment, the amount of liquid carrier is from 1 to 5 parts by weight relative to 1 part by weight of the crystalline 2'-cyano-2'-deoxy-$N^4$-palmitoyl-1-β-D-arabinofuranosylcytosine.

In an even more preferred embodiment, the amount of liquid carrier is from 2 to 5 parts by weight relative to 1 part by weight of the crystalline 2'-cyano-2'-deoxy-$N^4$-palmitoyl-1-β-D-arabinofuranosylcytosine.

In one highly preferred embodiment, the amount of liquid carrier is about 3 parts by weight relative to about 1 part by weight of the crystalline 2'-cyano-2'-deoxy-$N^4$-palmitoyl-1-β-D-arabinofuranosylcytosine.

In one highly preferred embodiment, the formulation comprises 25% w/w of active agent and 75 w/w of liquid carrier.

Another aspect of the invention relates to the use of a medium chain triglyceride as a liquid carrier in capsules of crystalline 2'-cyano-2'-deoxy-$N^4$-palmitoyl-1-β-D-arabinofuranosylcytosine.

Preferably, the medium chain triglyceride is fractionated coconut oil or caprilyic/capric triglyceride.

Yet another aspect of the invention relates to a liquid carrier for use in capsules of crystalline 2'-cyano-2'-deoxy-$N^4$- palmitoyl-1'-β-D-arabinofuranosylcytosine, wherein the liquid carrier is fractionated coconut oil or caprilyic/capric triglyceride.

Active Agent

The present formulation contains 2'-cyano-2'-deoxy-N 4-palmitoyl-1-β-D-arabinofuranosylcytosine as the active ingredient. This compound, also known as 1-(2-C-cyano-2-dioxy-β-D-arabino-pentofuranosyl)-N$^4$-palmitoyl cytosine, has the structure shown below and is referred to throughout as "CYC682".

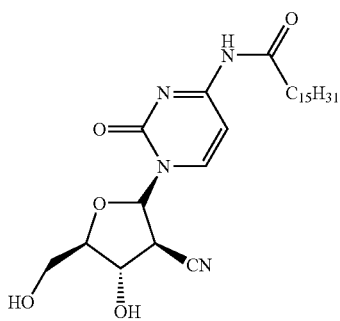

CYC682 was first disclosed in EP 536936 (Sankyo Company Limited; equivalent to JP 2569251) and was demonstrated to have excellent anti-tumour activity.

Subsequently, various crystal forms of CYC682 have been disclosed (see for example EP 1364959; European application derived from WO 02/64609 in the name of Sankyo Company Limited). These crystal forms exhibit improved storage stability and ease of handling, whilst retaining a desirable pharmacokinetic profile.

In one particularly preferred embodiment of the invention, the crystalline 2'-cyano-2'-deoxy-N$^4$-palmitoyl-1-β-D-arabinofuranosylcytosine comprises the B-form.

In one especially preferred embodiment, the crystalline 2'-cyano-2'-deoxy-N$^4$-palmitoyl-1-β-D-arabinofuranosylcytosine consists essentially of the B-form.

In one especially preferred embodiment, the crystalline 2'-cyano-2'-deoxy-N$^4$-palmitoyl-1-β-D-arabinofuranosylcytosine consists of the B-form.

The B-form of CYC682 can be prepared in accordance with the teachings of EP 1364959. CYC682 itself is prepared in accordance with the teachings of EP 536936.

By way of summary, 2'-cyano-2'-deoxy-1-β-D-arabinofuranosylcytosine monohydrochloride is passed through an ion-exchange resin (CHCOO$^-$ type) to form 2'-cyano-2'-deoxy-1-β-D-arabinofuranosylcytosine. This compound is subsequently reacted with 1,3-dichloro-1,1,3,3-tetraisopropyldisiloxane to form 2'-cyano-2'-deoxy-3',5'-O-(1,1,3,3-tetraisopropyldisiloxane-1,3-diyl)-1-β-D-arabinofuranosylcytosine, which is in turn reacted with palmitic acid to form 2'-cyano-2'-deoxy-N$^4$-palmitoyl-3',5'-O-(1,1,3,3-tetraisopropyldisiloxane-1,3-diyl)-1-β-D-arabinofuranosylcytosine. The final step involves deprotection using tetrabutylammonium fluoride to form the desired product, 2'-cyano-2'-deoxy-N$^4$-palmitoyl-1-β-D-arabinofuranosylcytosine (CYC682).

Alternatively, CYC682 can be prepared by reacting 2'-cyano-2'-deoxy-1-β-D-arabinofuranosylcytosine with palmitic anhydride.

The B form of CYC682 is prepared by adding methyl acetate containing water at approximately 2.5 vol % to CYC682 and heating to approximately 55° C. to prepare a clear solution. Subsequently, the solution is cooled under specific conditions and plate crystals are separated out of solution. After further stirring, the separated crystals are collected by filtration and washed with methyl acetate containing water at 2.5 vol % to afford the desired crystal B.

In one preferred embodiment, the pharmaceutical formulation is in unit dosage form. Preferably, the formulation comprises from about 0.1 to about 500 mg of the active agent, more preferably, from about 1 to about 200 mg, or more preferably still, from about 1 to about 100 mg of active agent.

In one highly preferred embodiment, the formulation comprises about 25 mg of active agent. In another highly preferred embodiment, the formulation comprises about 75 mg of active agent.

Process

As mentioned above, another aspect of the invention relates to a process for preparing a pharmaceutical formulation as described above which comprises the steps of:

(i) admixing crystalline 2'-cyano-2'-deoxy-N$^4$-palmitoyl-1-β-D-arabinofuranosyl-cytosine and a medium chain triglyceride;

(ii) transferring the mixture formed in step (i) into a preformed capsule; and (iii) sealing the capsule.

Preferably, the CYC682 is measured into a mixing vessel and the liquid carrier is added incrementally thereto until the correct amount has been added. The components are mixed using a commercially available mixer, for example, a Silverson mixer.

Preferably, the components are mixed at high speed for at least 2 minutes, more preferably, at least 3 minutes, even more preferably at least 5 minutes. In one especially preferred embodiment, the components are mixed for about 5 to about 8 minutes.

Ideally, the components are mixed until homogeneity is achieved. Once the mixture is homogenous, it is preferably degassed using a vacuum.

Preferably, the degassed mixture is transferred to the capsule using a capsule filler adjusted to give the desired fill weight. On completion, the capsules are sealed to prevent leakage. Various methods are available for sealing the capsules (see, for example, F. Wittner, "New Developments in Hermetic Sealing of Hard Gelatin Capsules", Pharm. Manuf. 2: 24-27, 1985).

In one preferred embodiment, step (iii) comprises sealing the gelatin capsule with a gelatin band. Typically, this involves rectifying the capsules and passing them once or twice over a wheel that revolves in a gelatin bath. A quantity of gelatin is picked up by the serrated wheel and applied to the junction of the cap and the body. The capsules remain in individual carriers for drying.

In an alternative preferred embodiment, step (iii) comprises sealing the gelatin capsule by microspraying. Typically, this involves sealing using a hydroalcoholic solution and uses the principle of lowering the melting point of gelatin by the application of moisture to the area between the capsule body and cap. The process involves spraying each capsule with a micro amount of sealing fluid at the body and cap junction using a directed fluid jet. Capillary action draws fluid up between the body and the cap. Drying then takes place by gently tumbling the capsules in a rotating drum. The process can be carried out using a commercially available machine such as a LEMS™ 30 (Liquid Encapsulation by MicroSpray; Capsugel Division of Warner Lambert Company).

The present invention is further described by way of Example.

EXAMPLES

Example 1

The B-form of CYC682 was prepared in accordance with the methodology described in EP 536936 and EP 1364959, both in the name of Sankyo Company Limited.

Preparation of CYC682 (in accordance with EP 536936)

1(a) 2'-Cyano-2'-deoxy-1-β-D-arabinofuranosylcytosine

A solution of 8.66 g (30 mmole) of 2'-cyano-2'-deoxy-1-β-D-arabinofuranosylcytosine monohydrochloride dissolved in 50 ml of water was passed through a column packed with 90 ml of Dowex 1×2 (trade name) ion-exchange resin (CHCOO⁻ type), and the column was washed with 300 ml of water. The effluent and the washings were combined and lyophilized, to give 7.23 g (yield 95.5%) of the title compound as a colourless powder.

NMR Spectrum (hexadeuterated dimethyl sulphoxide, 270 MHz) δ ppm:
7.28 (1H, broad singlet);
7.23 (1H, broad singlet);
7.83 (1H, doublet, J=7.8 Hz);
6.17 (1H, doublet, J=7.3 Hz);
6.17 (1H, doublet, J=5.9 Hz);
5.77 (1H, doublet, J=7.3 Hz);
5.12-5.16 (1H, multiplet);
4.36-4.44 (1H, multiplet);
3.56-3.80 (4H, multiplet).

1(1) 2'-Cyano-2'-deoxy-3',5'-O-(1,1,3,3-tetraisopropyldisiloxane-1,3-diyl)-1-β-D-arabinofuranosylcytosine 5.045 g (20 mmole) of 2'-cyano-2'-deoxy-1-β-D-arabinofuranosylcytosine [prepared as described in step (a) above] were dried three times by azeotropic distillation with pyridine, and the residue was suspended in 200 ml of pyridine. 6.7 ml (21 mmole) of 1,3-dichloro-1,1,3,3-tetraisopropyldisiloxane were added to the suspension, and the resulting mixture was stirred at room temperature for 1 hour in an atmosphere of nitrogen. The solution was concentrated to about one half of its original volume by distillation under reduced pressure, and the concentrate was diluted with 200 ml of ethyl acetate. The diluted solution was washed twice, each time with 200 ml of a saturated aqueous solution of sodium hydrogencarbonate. It was then dried over anhydrous magnesium sulphate. The solvent was removed by distillation under reduced pressure, and the resulting residue was mixed with a mixture of toluene and methanol. The mixture was subjected to azeotropic distillation, to give 11.21 g of a residue. This was purified by column chromatography through 300 g of silica gel (230-400 mesh), using methylene chloride containing 5% by volume methanol as the eluent, to give 8.67 g (yield 87%) of the title compound as a foam.

NMR (CDCl₃, 270 MHz) δ ppm:
7.69 (1H, doublet, J=7.26 Hz);
6.31 (1H, doublet, J=7.26 Hz);
5.74 (1H, doublet, J=7.26 Hz);
4.64 (1H, doublet of doublets, J=7.26 & 7.26 Hz);
4.15-4.04 (2H, multiplet);
3.84 (1H, doublet of triplets, J=7.26 & 3.30 Hz);
3.67 (1H, doublet of doublets, J=7.26 & 7.26 Hz);
1.15-0.93 (28H, multiplet).

1(c) 2'Cyano-2'-deoxy-N⁴-palmitoyl-3',5'-O-(1,1,3,3-tetraisopropyldisiloxanle-1,3-diyl)-1-β-D-arabinofuranosylcytosine A mixture of 1.48 g (3 mmole) of 2'-cyano-2'-deoxy-3',5'-O-(1,1,3,3-tetraisopropyldisiloxane-1,3-diyl)-1-β-D-arabinofuranosylcytosine [prepared as described in step (b) above] and 3.07 g (12 mmole) of palmitic acid was dried by azeotropic distillation using 50 ml of benzene, and the residue was dissolved in 30 ml of tetrahydrofuran. 2.47 g (12 mmole) of dicyclohexylcarbodiimide and 120 mg (0.9 mmole) of 4-(N,N-dimethylamino)pyridine were added to the solution, and the resulting mixture was stirred at 50° C. for 2.5 hours in an atmosphere of nitrogen. At the end of this time, the insoluble materials were removed by filtration, and the filtrate was freed from the solvent by distillation under reduced pressure. The residue was partitioned between 100 ml of ethyl acetate and 50 ml of a 5% w/v aqueous solution of sodium hydrogencarbonate. The organic layer was washed with 50 ml of a saturated aqueous solution of sodium chloride and dried over anhydrous magnesium sulphate. The solvent was distilled off under reduced pressure, and the residue was purified by column chromatography through silica gel, using methylene chloride containing 1% v/v methanol as the eluent, to give 1.85 g of the title compound as a caramel-like solid.

NMR Spectrum (hexadeuterated dimethyl sulphoxide, 270 MHz) δ ppm:
10.94 (1H, singlet);
8.02 (1H, doublet, J=7.82 Hz);
7.30 (1H, doublet, J=7.32 Hz);
6.21 (1H, doublet, J=7.83 Hz);
4.69 (1H, singlet);
4.22 (2H, multiplet);
3.98 (1H, doublet, J=2.45 Hz);
3.42 (1H, doublet, J=3.92 Hz);
2.40 (2H, triplet, J=7.32 Hz);
1.53 (2H, singlet);
0.82-1.23 (55H).

1(d) 2'-cyano-2'-deoxy-N⁴-palmitoyl-1-β-D-arabinofuranosylcytosine 0.31 ml (5.45 mmole) of acetic acid and 2.84 g (10.9 mmole) of tetrabutylammonium fluoride were added, whilst ice-cooling and stirring, to a solution of 4.0 g (5.45 mmole) of 2'-cyano-2'-deoxy-N⁴-palmitoyl-3',5'-O-(1,1,3,3-tetraisopropyldisiloxane-1,3-diyl)-1-β-D-arabinofuranosylcytosine [prepared as described in step (c) above] in 60 ml of tetrahydrofuran (which had previously been dried over molecular sieve 3A), and the resulting mixture was stirred for 40 minutes in an atmosphere of nitrogen. The reaction mixture was then concentrated to dryness by evaporation under reduced pressure, and the residue was partitioned between 100 ml of methylene chloride and 50 ml of a saturated aqueous solution of sodium chloride. The organic layer was washed with 50 ml of a saturated aqueous solution of sodium chloride and dried over anhydrous magnesium sulphate. The solvent was then removed by distillation under reduced pressure, and the residual caramel-like solid was purified by column chromatography through silica gel, using methylene chloride containing 4% v/v methanol as the eluent, to give 2.25 g of the title compound as a colourless powder.

NMR Spectrum (hexadeuterated dimethyl sulphoxide, 270 MHz) δ ppm:
10.91 (1H, singlet);
8.36 (1H, doublet, J=7.8 Hz);

7.29 (1H, doublet, J=7.8 Hz);
6.25 (1H, doublet, J=5.4 Hz);
6.21 (1H, doublet, J=7.3 Hz);
5.22 (1H, broad singlet);
4.43 (1H, multiplet);
3.61-3.93 (4H, multiplet);
2.40 (2H, triplet, J=7.3 Hz);
1.54 (2H, triplet, J=6.8 Hz);
1.24 (24H, singlet);
0.83-0.88 (3H, multiplet).

Alternative Preparation of 2'-cyano-2'-deoxy-$N^4$-palmitoyl-1-β-D-arabinofuranosyl cytosine A mixture of 12.9 g (51.1 mmole) of 2'-cyano-2'-deoxy-1-β-D-arabinofuranosylcytosine [prepared as described in Example 1(a) above] and 38.1 g (76.7 mmole) of palmitic anhydride was placed in a 1 litre round-bottomed flask, and 51 ml of dimethylformamide were added thereto. The resulting mixture was stirred in an oil bath kept at 100° C. for 20 minutes, whilst taking care to protect it from moisture. The disappearance of the starting compound was confirmed by thin layer chromatography (using methylene chloride containing 5% v/v methanol as the developing solvent). When the starting compound had disappeared, 513 ml of diisopropyl ether were added, whilst stirring, to the reaction mixture, and the mixture was allowed to stand for 1 hour, whilst ice-cooling. At the end of this time, insoluble materials were collected by filtration. The insoluble materials were completely dissolved in 513 ml of propanol by heating with stirring, and the solution was allowed to stand overnight in a refrigerator, to give 18.0 g of the title compound as a colourless powder, having the same physicochemical properties as the product of 1(d) above.

Example 2

Preparation of B-Form of CYC682 (in Accordance with EP 1364959)

(a) To 2'-cyano-2'-deoxy-$N^4$-palmitoyl-1-β-D-arabinofuranosylcytosine (30 g), which is the compound described in Example 1 (1d) of the Japanese Patent No. 2569251 and EP 536936 (described above in Example 1), was added methyl acetate containing water at 2.5 vol % (300 ml), and the resulting mixture was heated up to approximately 55° C. to prepare a clear solution. Subsequently, the solution was cooled to 5° C. at a rate of approximately 0.5° C. per minute. Upon cooling to about 45° C. in the course of the cooling, plate crystals were separated out of solution. After stirring furthermore at 5° C. for 20 minutes, the separated crystals were collected by filtration and washed with methyl acetate containing water at 2.5 vol % (30 ml) to afford the desired crystal B (28.78 g, purity 97.9%) in a 96.0% [N/N] yield.

(b) To 2'-cyano-2'-deoxy-$N^4$-palmitoyl-1-β-D-arabinofuranosylcytosine (8.7 kg), which is the compound described in Example 1 (1d) of the Japanese Patent No. 2569251 and EP 536936 (described above in Example 1), was added methyl acetate containing water at 1.9 vol % (80 L), and the resulting mixture was stirred at approximately 23° C. for 1.5 hr. The separated crystals were collected by filtration, washed with methyl acetate containing water at 1.9 vol % (20 L) and dried to afford the desired crystal B (7.7 kg, purity 97.3%) in a 90.1% [N/N] yield.

Example 3

Capsule Preparation

Capsules were prepared in two different strengths: 25 mg and 75 mg of CYC682. The higher strength was formulated to fill into a size 1 capsule, while the lower strength was formulated to fill into a size 3 capsule as appropriate. All materials are of pharmacopoeial quality.

The core formulation for both strengths contains:

| Ingredient | Function | % (w/w) |
| --- | --- | --- |
| CYC682 | active agent | 25 |
| Miglyol 812N Ph. Eur/GRAS | liquid carrier | 75 |

The core formulation is a simple suspension prepared by mixing the active agent with Miglyol 812N. Myglyol 812N is also known as fractionated coconut oil and is described in the Ph. Eur and is GRAS listed. These are the only ingredients in the formulation apart from the capsule shell and banding material.

White capsule shells were used containing titanium dioxide USP/Ph. Eur. 2% (by weight) and Gelatin USP/Ph. Eur to 100%. The capsules were banded at the join of the body and cap to prevent leakage. The band material contains Gelatin USP/Ph. Eur.

Both strengths of capsule are manufactured from the same mix with the doses being differentiated by differences in fill weight. The capsules are prepared as follows:
1. Weigh the CYC682 into the mixing vessel.
2. Add the Miglyol 812N incrementally until the correct total amount has been added.
3. Mix the two components using a Silverson mixer at high speed for 5-8 minutes.
4. Remove sample and check for homogeneity.
5. If homogeneous, draw a vacuum to degas the mixture.
6. Set up the Bosch 1500 L capsule filler with size 3 change parts and adjusts the filling pump to give the desired fill weight for the 25 mg dose.
7. Fill the 25 mg capsules using the following targets for average of 12 capsules i.e. Warning 2.5%; Action 3.5%; Reject 5.0%. The limits on the individual capsules are 7.5%.
8. Repeat for the 75 mg capsules by replacing the size 3 change parts with size 1 change parts and resetting the fill weights. All other conditions are the same.
9. On completion of all capsule filling the capsules are banded using clear gelatin.

The fill weights for the two strengths of capsules are 100 mg and 300 mg, respectively.

The capsule shells and the gelatin for banding were obtained from the following suppliers: Capsule—Capsulgel Bornem, Rijksweg 11, B-2880 Bornem, Belgium); Gelatin (for capsule banding)—Stoess A G, Gammelsbacherstr.2, 8412 Eberbach, Germany.

Example 4

Stability Tests

The capsules were set up in polypropylene containers at 40° C./75% relative humidity (RH) and 25° C./69% RH. The former is considered to constitute accelerated storage conditions while the latter is considered to constitute normal storage conditions. The study consisted of an initial evaluation under accelerated conditions for 6 months followed by a more prolonged evaluation under normal storage conditions. 6 months is the accepted duration for accelerated stability testing.

After 6 months under accelerated conditions and 18 months under normal storage conditions, the capsules showed no physical deterioration or any interaction with the packaging. Furthermore, HPLC analysis showed that there was no significant change in either the percentage of parent compound or in the percentage levels of (permitted) impurities over time.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A pharmaceutical formulation which comprises (i) a capsule, and (ii) a core comprising crystalline 2'-cyano-2'-deoxy-$N^4$-palmitoyl-1-β-D-arabinofuranosyl-cytosine and a liquid carrier, wherein the liquid carrier is a medium chain triglyceride oil or polyglycolized glyceride.

2. The pharmaceutical formulation according to claim 1 wherein the crystalline 2'-cyano-2'-deoxy-$N^4$-palmitoyl-1-β-D-arabinofuranosylcytosine comprises the B-form.

3. The pharmaceutical formulation according to claim 1 wherein the crystalline 2'-cyano-2'-deoxy-$N^4$-palmitoyl-1-β-D-arabinofuranosylcytosine consists essentially of the B-form.

4. The pharmaceutical formulation according to claim 1 wherein the medium chain triglyceride oil is fractionated coconut oil or caprilyic/capric triglyceride.

5. The pharmaceutical formulation according to claim 1 wherein the capsule is a gelatin capsule or a hard capsule.

6. The pharmaceutical formulation according to claim 1 wherein the capsule comprises one or more opacifying agents and/or one or more pigments.

7. The pharmaceutical formulation according to claim 6 wherein the pigments and/or opacifying agents are each present in an amount of about 0.1 to about 10%.

8. The pharmaceutical formulation according to claim 6 wherein at least one of the opacifying agents is titanium dioxide.

9. The pharmaceutical formulation according to claim 8 wherein the titanium dioxide is present in an amount of about 2%.

10. The pharmaceutical formulation according to claim 1 wherein the capsule is sealed by a gelatin band.

11. The pharmaceutical formulation according to claim 1 wherein the core consists essentially of crystalline 2'-cyano-2'-deoxy-$N^4$-palmitoyl-1-β-D-arabinofuranosylcytosine and the liquid carrier.

12. The pharmaceutical formulation according to claim 1 wherein the amount of liquid carrier is from 2 to 50 parts by weight relative to 1 part by weight of the crystalline 2'-cyano-2'-deoxy-$N^4$-palmitoyl-1-β-D-arabinofuranosylcytosine.

13. The pharmaceutical formulation according to claim 1 wherein the amount of liquid carrier is from 2 to 10 parts by weight relative to 1 part by weight of the crystalline 2'-cyano-2'-deoxy-$N^4$-palmitoyl-1-β-D-arabinofuranosylcytosine.

14. The pharmaceutical formulation according to claim 1 wherein the amount of liquid carrier is from 2 to 5 parts by weight relative to 1 part by weight of the crystalline 2'-cyano-2'-deoxy-$N^4$-palmitoyl-1-β-D-arabinofuranosylcytosine.

15. The pharmaceutical formulation according to claim 1 wherein the amount of liquid carrier is about 3 parts by weight relative to about 1 part by weight of the crystalline 2'-cyano-2'-deoxy-$N^4$-palmitoyl-1-β-D-arabinofuranosylcytosine.

16. The pharmaceutical formulation according to claim 1 which is for oral administration.

17. A method for preparing a pharmaceutical formulation according to claim 1 which comprises the steps of:
   (i) admixing crystalline 2'-cyano-2'-deoxy-$N^4$-palmitoyl-1-β-D-arabinofurano-sylcytosine and a medium chain triglyceride;
   (ii) transferring the mixture formed in step (i) into a preformed capsule; and
   (iii) sealing the capsule.

18. The method according to claim 17 wherein step (iii) comprises sealing the capsule with a gelatin band.

19. The method according to claim 17 wherein step (iii) comprises sealing the capsule by microspraying.

* * * * *

UNITED STATES PATENT AND TRADEMARK OFFICE
CERTIFICATE OF CORRECTION

PATENT NO. : 8,497,291 B2  
APPLICATION NO. : 12/097912  
DATED : July 30, 2013  
INVENTOR(S) : Westwood et al.

Page 1 of 1

It is certified that error appears in the above-identified patent and that said Letters Patent is hereby corrected as shown below:

On the title page item [75] delete "Alistair Selkirk" and insert --Alastair Selkirk--.

Signed and Sealed this
Twelfth Day of November, 2013

Teresa Stanek Rea
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,497,291 B2 |
| APPLICATION NO. | : 12/097912 |
| DATED | : July 30, 2013 |
| INVENTOR(S) | : Westwood et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1121 days.

Signed and Sealed this
Twenty-seventh Day of January, 2015

Michelle K. Lee
*Deputy Director of the United States Patent and Trademark Office*